United States Patent [19]

Glenn, Jr.

[11] 4,046,220
[45] Sept. 6, 1977

[54] METHOD FOR DISTINGUISHING BETWEEN SINGLE-PHASE GAS AND SINGLE-PHASE LIQUID LEAKS IN WELL CASINGS

[75] Inventor: Edwin E. Glenn, Jr., Dallas, Tex.

[73] Assignee: Mobil Oil Corporation, New York City, N.Y.

[21] Appl. No.: 668,895

[22] Filed: Mar. 22, 1976

[51] Int. Cl.² .................. G01V 1/40; E21B 47/12
[52] U.S. Cl. .................. 181/105; 340/15.5 A; 181/102; 73/155
[58] Field of Search .................. 340/15.5 BH, 15.5 A, 340/15.5 AC; 181/102, 105, 125; 175/48; 73/40.5 A, 155; 324/2

[56] References Cited

U.S. PATENT DOCUMENTS

| 2,210,417 | 8/1940 | McKinley | 340/15.5 A |
|---|---|---|---|
| 2,396,935 | 3/1946 | Walstrom | 340/15.5 AC |
| 3,509,764 | 5/1970 | Baldwin et al. | 73/155 |
| 3,588,800 | 6/1971 | Moore | 340/15.5 BH |
| 3,816,773 | 6/1974 | Baldwin et al. | 73/194 A |
| 3,854,323 | 12/1974 | Hearn et al. | 73/155 |
| 3,908,454 | 9/1975 | Mullins et al. | 181/102 |
| 3,908,761 | 9/1975 | Patterson et al. | 73/155 |
| 3,930,556 | 1/1976 | Kusuda et al. | 73/194 A |

OTHER PUBLICATIONS

McKinley et al., "The Structure and Interpretation of Noise from Flow Behind Cemented Casing," 1972, 12pp, 47th Annu. SPE of AIME Fall Mtg., Preprint No. SPE-3999.

Primary Examiner—Nelson Moskowitz
Attorney, Agent, or Firm—C. A. Huggett; George W. Hager, Jr.

[57] ABSTRACT

An acoustic detector is moved through a well to detect sound at various levels within the well. An electrical signal indicative of the detected sound is applied from the acoustic detector by way of a conductor cable to uphole recording equipment including an amplifier, spectrum analyzer, and recorder. The spectrum analyzer provides a frequency spectrum of the amplified signal from the acoustic detector. This frequency spectrum is recorded for use in the identification of flow leaks through or behind the casing of the well in accordance with predetermined spectrum analysis characteristics of single-phase gas and single-phase liquid leaks.

15 Claims, 3 Drawing Figures

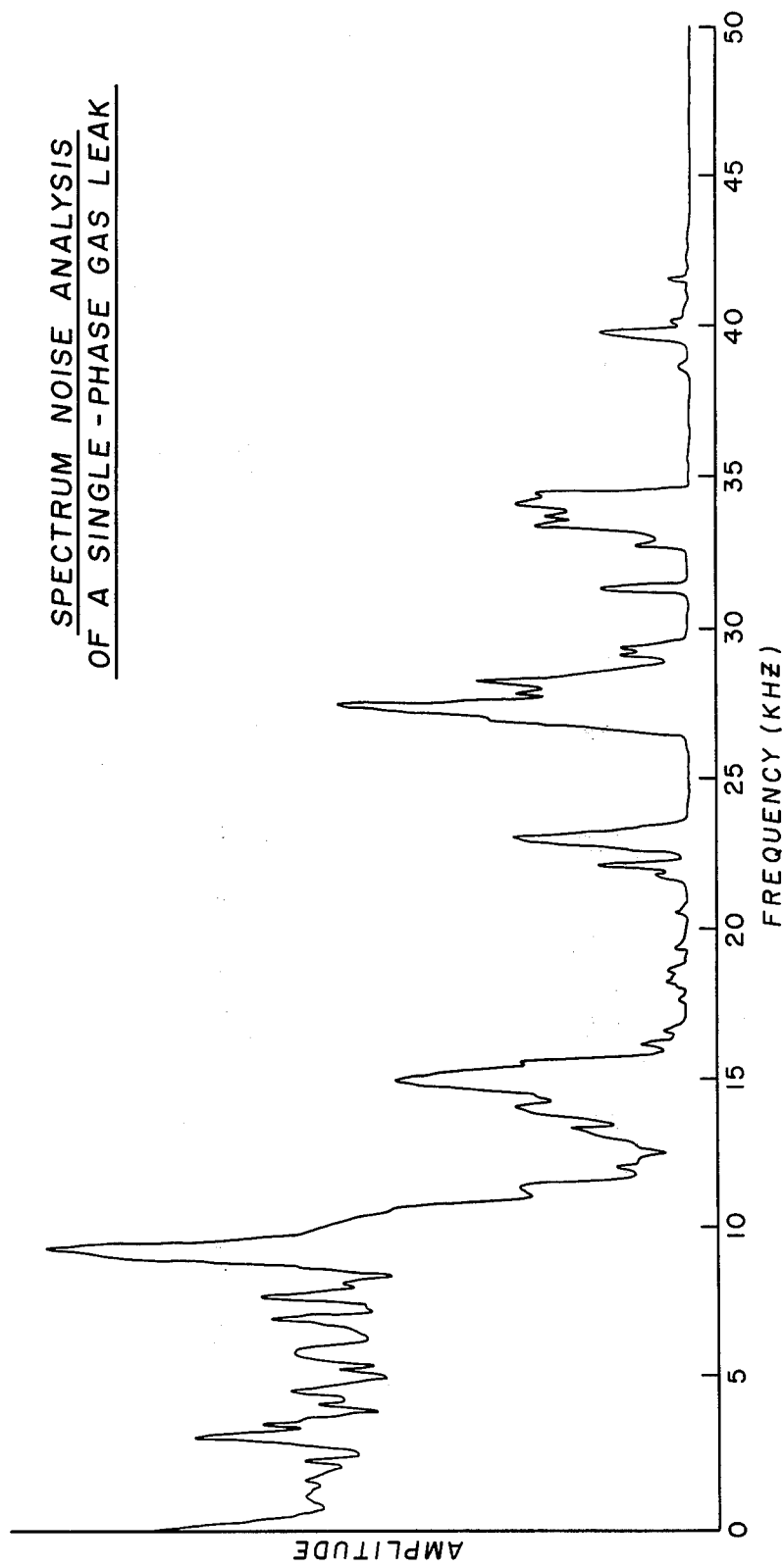

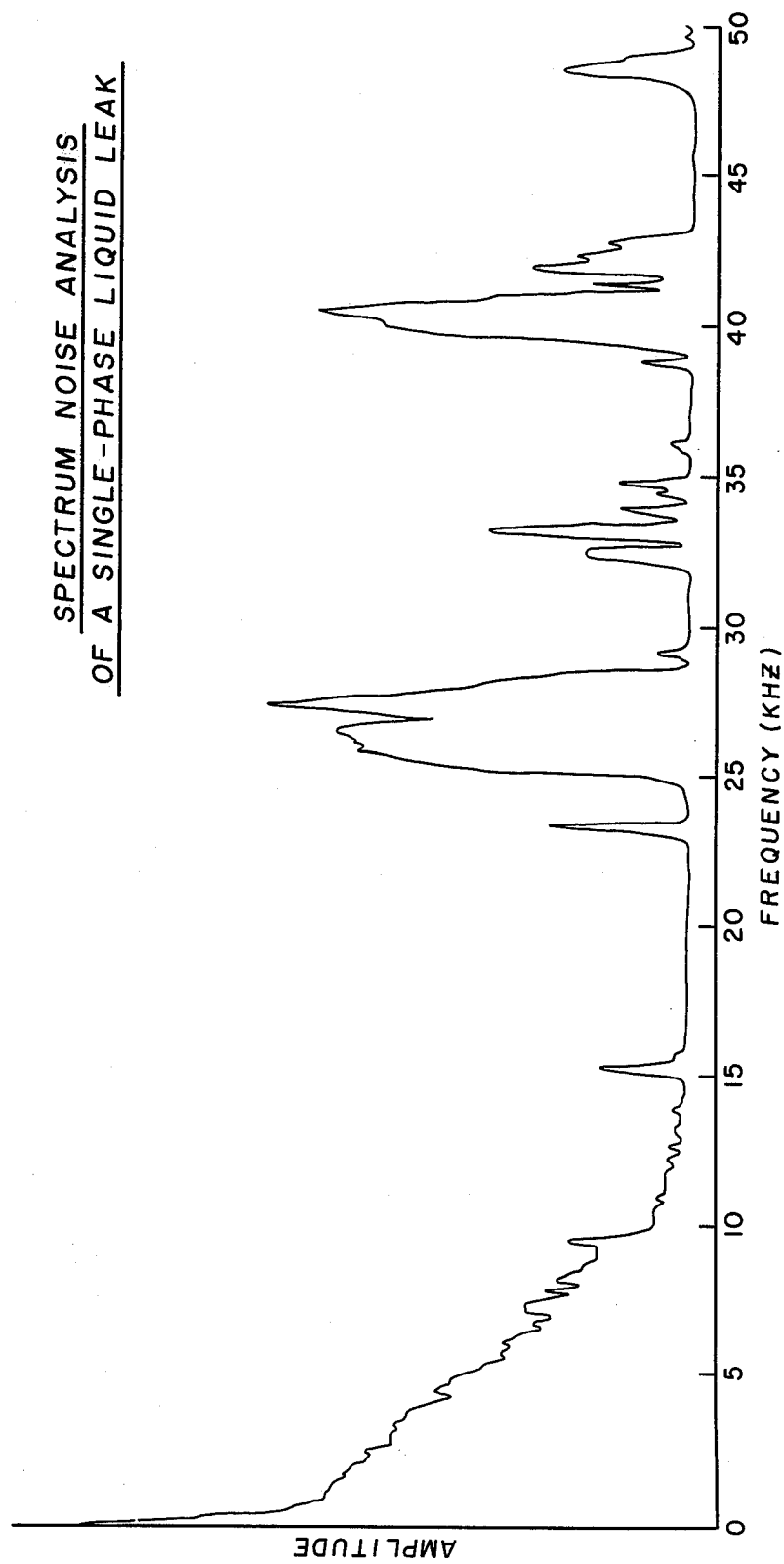

METHOD FOR DISTINGUISHING BETWEEN SINGLE-PHASE GAS AND SINGLE-PHASE LIQUID LEAKS IN WELL CASINGS

BACKGROUND OF THE INVENTION

This invention relates generally to acoustic well logging and more particularly to the detection of flow leaks through or behind the casing of a well penetrating the subsurface formations.

Acoustical noise logging of wells to determine the location of fluid flow thereinto it well known in the art. For example, in U.S. Pat. No. 2,210,417 to Kinley, leaks through casing are located by determining the location of sound produced by liquid passing through openings in the casing. A sound detector is moved through a well and is connected to an uphole indicating device or recording means. The intensity of sound produced by liquids passing through the casing is thus indicative of leaks in the casing, and location of such leaks is readily discernible from a graphical record of intensity versus the depth of the sound detector within the well. A similar method of determining the location of fluid flow into a well is disclosed in U.S. Pat. No. 2,396,935 to Wahlstrom.

A noise-logging technique for distinguishing single-phase flow from two-phase flow leaks through or behind the casing leaks is described in "The Structure and Interpretation of Noise From Flow Behind Cemented Casing," by R. M. McKinley, F. M. Bower, and R. C. Rumble, JOURNAL OF PETROLEUM TECHNOLOGY, March, 1973, pp. 329-338. The source of the leak is located from a noise-amplitude log and the type of leak (single- or two-phase flow) is determined from a spectrum of the noise source. A single-phase flow leak is one in which water is throttling into water or air is throttling into air. A two-phase flow is one in which air is throttling into water. The above-described article presents experimental results indicating that two-phase leaks have a noise-frequency structure distinguishable from that for single-phase leaks by a larger noise level in the band of 200 to 600 hertz. At higher frequencies, both single- and two-phase leaks have a noise characteristic of free-stream turbulence and are indistinguishable above 1,000 hertz.

SUMMARY OF THE INVENTION

In a method of distinguishing between single-phase gas and single-phase liquid leaks through or behind the casing of a well, the acoustic noise generated by the casing leak is monitored within the well and the spectrum analysis of such acoustic noise is measured uphole. The noise levels of such measured spectrum analysis is compared with predetermined spectrum analysis noise level characteristics for single-phase gas and single-phase liquid leaks to distinguish the type of leak through or behind the casing of the well as either a single-phase gas leak or a single-phase liquid leak.

More particularly, a reference frequency is identified above which the noise level characteristics of said predetermined spectrum analysis is decreased for a single-phase gas leak and is about the same or increased for a single-phase liquid leak. The casing leak is identified as a single-phase gas leak if the noise level of the measured spectrum analysis at frequencies above the reference frequency is decreased from the noise level of the measured spectrum analysis at the reference frequency. The casing leak is identified as a single-phase liquid leak if the noise level of the measured spectrum analysis at frequencies above the reference frequency is about the same or increased from the noise level of the measured spectrum analysis at the reference frequency. In one aspect of the invention, this reference frequency is in the order of 1 to 10 kilohertz.

BRIEF DESCRIPTION OF THE DRAWINGS

FIGS. 2 and 3 illustrate the spectrum analysis for both single-phase gas and single-phase liquid leaks, respectively, through or behind the casing of a well as would be measured by the spectrum analyzer of FIG. 1.

DESCRIPTION OF THE PREFERRED EMBODIMENT

Figure 1:
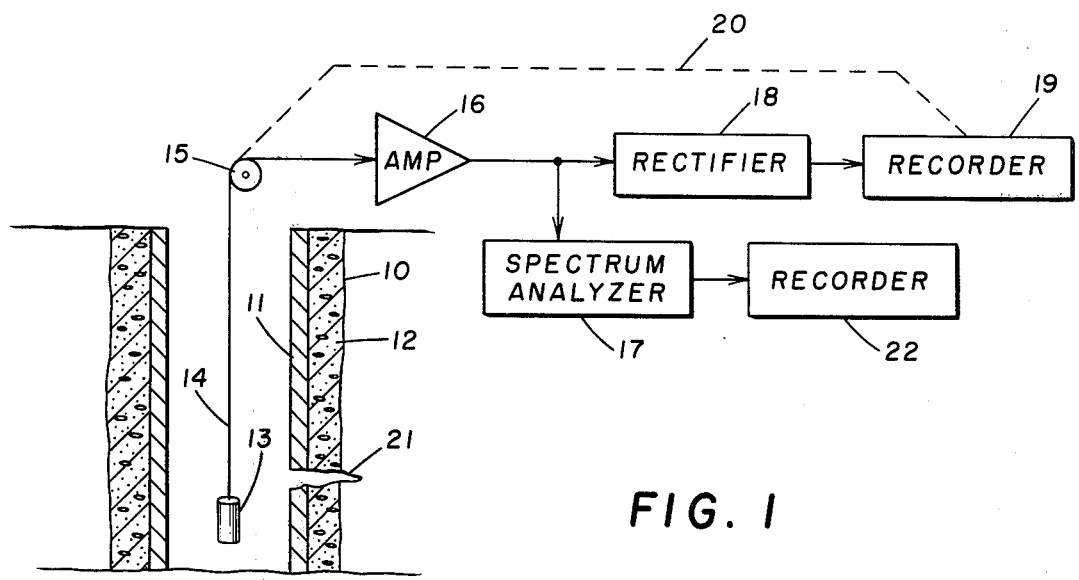
FIG. 1 illustrates an acoustic logging system of the present invention for distinguishing between single-phase gas and single-phase liquid leaks through or behind the casing of a well.

Referring to FIG. 1, there is illustrated an acoustic noise logging system employed for carrying out the method of the present invention. A well 10 traverses the subsurface formations. A well casing 11 is cemented in place with a cement sheath 12. An acoustic detector 13 is suspended in the well by a conductor cable 14 which passes over the sheave 15 to the uphole recording equipment. In one mode of operation, the acoustic detector 13 is moved through the well to detect sound at various levels within the well. Acoustic detector 13 comprises an electroacoustic transducer and amplifier of conventional acoustic logging tool design. The electrical signal from acoustic detector 13 is applied by way of the conductor cable 14 to the surface amplifier 16 of the uphole recording equipment. The output of amplifier 16 is applied through the rectifier 18 to the recorder 19. The recorder 19 is a strip chart recorder of the conventional type used with acoustic logging equipment. It includes a moving pen or recording element and a recording medium such as paper. The recording medium is moved relative to the recording pen in correlation with the depth of the acoustic detector 13 by means of an electromechanical linkage 20 coupled to the sheave 15 over which the conductor cable 14 passes. As the acoustic detector 13 is moved along the well, recorder 19 produces a log or trace of the amplitude of the sound detected in the well. As the acoustic detector 13 passes a leak through or behind the casing 11 and cement sheath 12, such as indicated by the through casing leak at 21, for example, the noise created by any liquid or gas flow through the casing leak from the formation into the well is detected by the acoustic detector 13 and sent by way of the conductor cable 14 to the uphole recording equipment. The received acoustic signal is recorded on the recorder 19 in correlation with depth as an indication of the location of the downhole leak.

Once the casing leak has been identified and located, it becomes desirable to identify the type of leak. It is therefore a specific aspect of the present invention to provide for a method by which the identification of the flow leak through or behind the casing can be distinguished as a single-phase gas leak or a single-phase liquid leak. In accordance with this aspect of the present invention, the electrical signal from the downhole acoustic detector 13 is amplified by the uphole amplifier 16 and passed through a spectrum analyzer 17. The output of spectrum analyzer 17 is recorded on a conventional X-Y plotter 22 to provide a frequency spectrum of the amplified signal from the acoustic detector 13. It has been discovered that even though single-phase gas and single-phase liquid leaks may exhibit similar frequency spectrum characteristics, they can be distinguished from one another on the basis of their respective noise levels. Accordingly, noise amplitude analysis of the various frequency components of the amplified signal from the acoustic detector 13 can be made to distinguish the type of casing leak.

In one embodiment, the acoustic detector 13 is a lead-zirconate-titanate piezoelectric ceramic transducer No. 5500 of Channel Industries, Inc., for example, and the spectrum analyzer 17 is the Nicolet Scientific UA500, for example. FIG. 2 illustrates a graph of noise amplitude against the frequency spectrum for a single-phase gas leak derived from this particular embodiment in the frequency range of up to 50 kilohertz for a gas leak of air throttling into an air-filled annulus at a pressure differential times flow rate of 153,000 (psi) (cu.ft./day).

FIG. 3 illustrates a graph of noise amplitude against the frequency spectrum for a single-phase liquid leak also derived from this particular embodiment in the frequency range up to 50 kilohertz for a fluid leak of water throttling into a water-filled annulus at a pressure differential times flow rate of 37,000 (psi) (cu.ft./day).

It can be seen from the frequency spectra of FIGS. 2 and 3 that the noise levels for both single-phase gas and single-phase liquid leaks exhibit identifiable peaks in their respective frequency spectra at select frequencies above about 1 to 10 kilohertz. It can further be seen from the frequency spectra of FIGS. 2 and 3 that the noise level peaks for a gas leak at frequencies above about 9 to 10 kilohertz are less than the noise level peak for the same gas leak at about 9 to 10 kilohertz, while the noise level peaks for a liquid leak at frequencies above about 9 to 10 kilohertz are about the same or greater than the noise level peak for the same liquid leak at about 9 to 10 kilohertz.

Thus, having identified the reference frequency range above which a gas leak is generally characterized by a decrease in noise level and a liquid leak is generally characterized by an increase in noise level and by obtaining a record of the noise amplitude of the frequency spectrum from the downhole acoustic transducer, a detected casing leak can be identified in accordance with the present invention as a single-phase gas or single-phase liquid leak.

It can be further seen from FIGS. 2 and 3 that several of the noise level peaks above the 9 - to 10-kilohertz frequency range are quite distinct. For example, in FIG. 2 the gas leak noise peaks are found to occur at frequencies of about 18, 22–23, 27–29, 32–34, and 37 kilohertz. In FIG. 3, the liquid leak noise peaks are found to occur at frequencies of about 23, 27, 29–31, 33, 37, 39–40, 42, and 48 kilohertz. The remaining identifiable noise peaks in FIGS. 2 and 3 have been found to be associated with resonance of the particular acoustic detector utilized in the embodiment as described above.

Although the present invention has been described in connection with one embodiment, various modifications and changes can be made. For example, it might be desirable to employ an acoustic detector having a different sensitivity than that described with the particular embodiment herein. Also, variable temperature and pressure conditions might be encountered within the well. Such changes in the acoustic detector and within the well conditions can cause variations in the noise frequency spectra from that illustrated in FIGS. 2 and 3 without departing from the spirit and scope of the present invention as set forth in the appended claims.

I claim:

1. A method of distinguishing between single-phase gas and single-phase liquid leaks through or behind the casing of a well, comprising the steps of:
   a. monitoring acoustic noise generated by a casing leak within a well,
   b. producing an electrical signal representative of said monitored acoustic noise,
   c. measuring the frequency spectrum of said electrical signal,
   d. selecting a reference frequency within said measured frequency spectrum above which a single-phase gas leak exhibits at first select frequencies noise peaks having decrease in amplitude from the amplitude of the noise peak at said reference frequency and a single-phase liquid leak exhibits at second select frequencies noise peaks having no change or an increase in amplitude from the amplitude of the noise peak at said reference frequency,
   a. comparing the amplitudes of the noise peaks of said acoustic noise at said reference frequency and at said first and second select frequencies above said reference frequency,
   f. identifying said casing leak as a single-phase gas leak if the amplitude of the noise peaks at said first select frequencies are decreased from the amplitude of the noise peak at said reference frequency, and
   g. identifying said casing leak as a single-phase liquid leak if the amplitude of the noise peaks at said second select frequencies is the same or is increased from the amplitude of the noise peak at said reference frequency.

2. The method of claim 1 wherein said reference frequency is in the order of 10 kilohertz.

3. The method of claim 1 wherein one of said first select frequencies for identifying a single-phase gas leak is in order of 18 kilohertz.

4. The method of claim 1 wherein one of said first select frequencies for identifying a single-phase gas leak is in the order of 22 to 23 kilohertz.

5. The method of claim 1 wherein one of said first select frequencies for identifying a single-phase gas leak is in the order of 27 to 29 kilohertz.

6. The method of claim 1 wherein one of said first select frequencies for identifying a single-phase gas leak is in the order of 32 to 34 kilohertz.

7. The method of claim 1 wherein one of said first select frequencies for identifying a single-phase gas leak is in the order of 37 kilohertz.

8. The method of claim 1 wherein one of said second select frequencies for identifying a single-phase liquid leak is in the order of 23 kilohertz.

9. The method of claim 1 wherein one of said second select frequencies for identifying a single-phase liquid leak is in the order of 27 kilohertz.

10. The method of claim 1 wherein one of said second select frequencies for identifying a single-phase liquid leak is in the order of 29 to 31 kilohertz.

11. The method of claim 1 wherein one of said second select frequencies for identifying a single-phase liguid leak is in the order of 33 kilohertz.

12. The method of claim 1 wherein one of said second select frequencies for identifying a single-phase liquid leak is in the order of 37 kilohertz.

13. The method of claim 1 wherein one of said second select frequencies for identifying a single-phase liquid leak is in the order of 39 to 40 kilohertz.

14. The method of claim 1 wherein one of said second select frequencies for identifying a single-phase liquid leak is in the order of 42 kilohertz.

15. The method of claim 1 wherein one of said second select frequencies identifying a single-phase liquid leak is in the order of 48 kilohertz.

* * * * *